US007988986B2

(12) United States Patent
Beisang et al.

(10) Patent No.: US 7,988,986 B2
(45) Date of Patent: Aug. 2, 2011

(54) IMPLANT FILLING MATERIAL AND METHOD

(76) Inventors: Arthur A. Beisang, White Bear Lake, MN (US); Robert A. Ersek, Austin, TX (US); Arthur A. Beisang, III, North Oaks, MN (US); Daniel J. Beisang, North Oaks, MN (US)

( * ) Notice: Subject to any disclaimer, the term of this patent is extended or adjusted under 35 U.S.C. 154(b) by 0 days.

(21) Appl. No.: 12/434,764

(22) Filed: May 4, 2009

(65) Prior Publication Data
US 2009/0214611 A1 Aug. 27, 2009

Related U.S. Application Data

(63) Continuation-in-part of application No. 11/450,644, filed on Jun. 9, 2006, now abandoned, which is a continuation-in-part of application No. 10/839,559, filed on May 5, 2004.

(60) Provisional application No. 60/533,168, filed on Dec. 30, 2003.

(51) Int. Cl.
*A61F 13/00* (2006.01)
*A61F 2/52* (2006.01)
*A61F 2/12* (2006.01)
*A61K 9/14* (2006.01)

(52) U.S. Cl. ........ 424/422; 424/423; 424/484; 424/486; 623/7; 623/8

(58) Field of Classification Search .................. None
See application file for complete search history.

(56) References Cited

U.S. PATENT DOCUMENTS

| | | | |
|---|---|---|---|
| 2,938,017 A | 5/1960 | Grosser | |
| 3,759,880 A | 9/1973 | Hoffman et al. | |
| 3,933,766 A | 1/1976 | Hofmann et al. | |
| 4,731,081 A * | 3/1988 | Tiffany et al. | 623/8 |
| 4,828,827 A * | 5/1989 | Henderson et al. | 424/78.18 |
| 5,067,965 A * | 11/1991 | Ersek et al. | 623/66.1 |
| 5,156,601 A | 10/1992 | Lorenz et al. | |
| 5,258,028 A | 11/1993 | Ersek et al. | |
| 5,258,421 A | 11/1993 | Lorenz et al. | |
| 5,306,504 A | 4/1994 | Lorenz | |
| 5,480,430 A | 1/1996 | Carlisle et al. | |
| 5,571,182 A | 11/1996 | Ersek et al. | |
| 5,997,574 A | 12/1999 | Hayes et al. | |
| 6,099,565 A | 8/2000 | Sakura, Jr. | |
| 6,153,664 A | 11/2000 | Wise et al. | |
| 6,410,044 B1 | 6/2002 | Chudzik et al. | |
| 6,465,001 B1 | 10/2002 | Hubbell et al. | |
| 6,497,729 B1 * | 12/2002 | Moussy et al. | 623/23.57 |
| 6,783,546 B2 | 8/2004 | Zucherman et al. | |
| 6,955,690 B1 | 10/2005 | Cao | |
| 7,316,822 B2 | 1/2008 | Binette et al. | |

FOREIGN PATENT DOCUMENTS
WO  WO 0153359 A1 * 7/2001

OTHER PUBLICATIONS
Search Report dated Jan. 28, 2011.

* cited by examiner

*Primary Examiner* — Fereydoun G Sajjadi
*Assistant Examiner* — Casey Hagopian
(74) *Attorney, Agent, or Firm* — Nikolai & Mersereau, P.A.; C. G. Mersereau

(57) ABSTRACT

Compositions of cross-linked polyvinylpyrrolidone (PVP) are disclosed that are generally in the form of an elastic, hydrophilic, water-insoluble viscous cohesive mass of material that has many important medical uses including uses as a filler for implants. The present invention also involves a process for producing such compositions.

12 Claims, No Drawings

IMPLANT FILLING MATERIAL AND METHOD

CROSS-REFERENCED TO RELATED APPLICATIONS

The present application is a Continuation-In-Part of co-pending application Ser. No. 11/450,644, filed on Jun. 9, 2006 which, in turn, is a Continuation-In-Part of application Ser. No. 10/839,559, filed on May 5, 2004, the entirety, both of which, are incorporated herein by reference for any purpose. application Ser. No. 10/839,559, in turn, claims priority based on Provisional Application No. 60/533,168, filed Dec. 30, 2003, which is hereby also incorporated herein by reference in its entirety.

STATEMENT REGARDING FEDERALLY SPONSORED RESEARCH OR DEVELOPMENT

Not applicable

BACKGROUND OF THE INVENTION

I. Field of the Invention

The present invention relates generally to medical implants and, more particularly, to implantable prostheses and materials used for same. The invention also relates to a process for making such materials.

II. Related Art

Medically implantable prostheses, exemplified by breast implants, are well known in the art. Such implants generally comprise a formed body presenting a nonreactive, biocompatible outer surface to surrounding tissue following implantation. Fluid-filled medical implants generally comprise a viscous fluid contained within an elastomeric shell. It has been observed that fluid-filled medical implants may leak or rupture following implantation and require explanation. The escaping fluid filler material may be contained within a periprosthetic capsule that forms around the prostheses after implantation, or it may be released into the body. It would present a desirable advantage to provide a filler for an implantable soft tissue prosthesis wherein the filler itself is substantially cohesive to facilitate removal of the filler from the body in the event of a rupture. It would present an additional advantage were this material composition nontoxic and preferably bioabsorbable.

Filling materials disclosed in previous patents relating to breast implants containing the polymer polyvinylpyrrolidone (PVP) have had some drawbacks that have been demonstrated and reported in the cosmetic plastic surgery literature. These implants generally are constructed with a silicone membrane shell. These drawbacks relate to the osmotic pressure created within the silicone shell membrane of the breast implant by the PVP solutions that have been previously utilized as filling material in clinical settings. The drawbacks also relate to control of the viscosity, cohesiveness, and elasticity of the PVP mixture used for filling breast implants.

Cross-linked PVP has a history of patented processes for the preparation of cross-linked PVP products, now commercially available from two major corporations: ISP and BASF. Three such patents are U.S. Pat. Nos. 2,938,017, 3,759,880, and 3,933,766. In the previous literature describing the process for obtaining cross-linked PVP, the temperature at which the cross-linking of PVP occurred has been required to be 100° C. or higher. Known processes for cross-linking PVP have required compounds or conditions which make them difficult to control. The rapid rate of cross-linking PVP in the aforementioned patents prohibits precise control of the cross-linked PVP products. Prior processes including that described in U.S. Pat. No. 3,933,766 call for the use of a cross-linking compound such as a cyclic acid amide or alkoxides in high pH environments (10-12 pH) or special commercial chemical "cross-linkers" at temperatures of 150° C. and pressures of 100 mm Hg.

Tacky, hydrophilic gel dressings have been disclosed using poly(N-vinyl lactam)-urethane gels in which the poly (N-vinyl lactam) may be polyvinylpyrrolidone (PVP) in U.S. Pat. Nos. 5,156,601 and 5,258,421. A skin adhesive hydrogel formed by mixing high molecular weight PVP having ring opened pyrrolidone groups and a multi-functional amine-containing polymer is disclosed in U.S. Pat. No. 5,306,504.

A further patent to Hayes et al, U.S. Pat. No. 5,997,574, discloses a medical implant which includes a shell and a filler material in which the filler material requires a combination of materials, namely, both a Theological agent and an osmotic control agent that is different from the Theological agent. In particular, Hayes et al teaches the use of polyvinylpyrrolidone (PVP) as an osmotic control agent in combination with a gum, preferably guar gum, as the Theological control agent. The combination is considered essential in order to provide a filler material having the desired properties for a breast implant, for example. The filler material of Hayes et al, further, is a one-phase, water-soluble mixture.

A long-standing need in the art for an improved formulation of PVP mixture for a filling material in breast implants has been recognized by the inventors and a new formula has been compounded and proposed. Accordingly, one aspect of the present invention relates to an improvement in cohesiveness, osmolarity, elasticity, and the viscosity of cross-linked PVP mixtures and mixtures of cross-linked PVP derivatives so that they can be controlled to be more favorable as filling material for breast implants and other uses. The proposed material composition is a viscous, highly elastic and cohesive mass comprised primarily in one embodiment of a lattice of water-insoluble, heat-treated, cross-linked PVP and water.

SUMMARY OF THE INVENTION

According to the present invention, there is provided a composition of cross-linked PVP that is in the form of an elastic, hydrophilic, water-insoluble viscous cohesive mass of material that has many important medical uses. The present invention also involves a process for forming such a composition.

By way of definition, as used herein, the term "cohesive mass" refers to a unitary body composed of a pliant material, wherein when the unitary body is subjected to an external force directed toward disrupting the cohesive structural integrity of the unitary body, the unitary body resists fragmentation and retains its structural integrity.

Thus, the cohesive mass is a material consisting essentially of an aqueous solution of a single polymeric agent and a base and is preferably in the form of a hydrogel, or the like, that possesses generally gel-like elastic properties. Hydrogels, or water-containing gels, are defined as polymers characterized by hydrophilicity and insolubility in water. In water, they swell to an equilibrium volume, but preserve their shape, the hydrophilicity being due to the presence of water-solubilizing groups and the stability of the shape due to the presence of a three-dimensional network. Most preferably, the compositions of the cohesive mass of the present invention consist essentially of materials which are insoluble in water, but which are able to imbibe water to achieve a maximum, stabilized volume without loss of shape or mechanical strength.

They further do not require additional rheological agents such as gums to operate successfully as filler materials for medical implants. Thus, the filler materials of the present invention may also be said to be free of separate rheological control agents that characterize certain earlier filler materials. Smaller trace amounts of other materials may be present which do not affect the essential properties of the stable gel-like mass. Thus, the cohesive mass may be said to consist essentially of a hydrogel and may be referred to as such. Also, the composition may be referred to as cross-linked PVP and may include chemically modified PVP or PVP derivatives which result from a process of the invention.

According to an aspect of the present invention, it has been discovered that under prescribed circumstances, a product in the form of a high quality water-insoluble, elastic cohesive mass product can also be obtained without a heat-treatment step.

The process involves reacting a mixture consisting essentially of a water solution of PVP and a minor amount of a basic material such as sodium hydroxide (NaOH), for example, at ambient temperature and pressure for a sufficient time to produce the desired amount of reaction in the PVP. This results in a cross-linked or otherwise modified PVP polymer mass which can be described as cross-linked PVP or a modified PVP or a PVP derivative as the exact chemical structure is not known. The viscosity of fully processed material has been observed to be about 15,000 to 45,000 centipoise. One material was observed to be a 42% lattice of water-insoluble, cross-linked PVP and water.

In accordance with one preferred process, a known minor amount (weight) of solid sodium hydroxide (NaOH) base is dissolved in a known amount by weight of water and a known amount by weight of polyvinylpyrrolidone (PVP) such as K 29/32 Plasdone (PVP), which is one of many PVP products readily available commercially, is added and the solution is thoroughly mixed and allowed to react at ambient temperature and pressure for about 20 to 60 hours during which time a water-insoluble cohesive mass or hydrophilic cohesive gel mass is formed. An amount of water is added to the water-insoluble gel mass to maximize and stabilize the final volume of the gel mass. The final equilibrium or stabilized volume is reached in about 40 hours or less and requires from about 25-30% by weight of water.

The maximized, stabilized reacted mass may then be neutralized in an aqueous acid or base solution, as necessary. The strength of the acid or base solution is preferably such that the pH of the neutralized, stabilized material is close to neutral. Any remaining solution can be decanted off and in a well known manner. Preferred acids include HCl and NaOH is the preferred base. Alternatively aqueous HCl or NaOH solution may be used to stabilize the water-insoluble gel mass to accomplish stabilization and neutralization in a single step.

The cohesive gel mass of the above process may normally be basic and the mass treated using a neutralizing aqueous acid solution that may have a pH of about 1.0 or less. It has been discovered that the cohesive water-insoluble gel mass of the invention is extremely chemically inert and the basic characteristics of the gel produced by the process of the invention are not altered by exposure to either very strong base or very strong acids.

After treatment with the acid solution, the cohesive mass or gel normally shows a stabilized pH of about 7±0.6 with the affinity to absorb water having been fully satisfied (i.e., the equilibrium maximum or stabilized volume reached).

The term "minor amount" generally refers to less than one percent (w/w) with respect to the amount of PVP and the ratio of the amount of base (NaOH) to PVP may be as little as 0.1%.

It has also been found that the weight of PVP should be preferably above about 65% to about 80% of the weight of water. More preferably, the weight of PVP is a minimum of 72% of the weight of water and most preferably is about 75%.

In accordance with the process of the invention, it has been found that a water-insoluble viable cohesive mass suitable for implants closely mimicking breast or other bodily tissue can be produced. The material has a mass and pH similar to natural biological materials and is radiolucent. The reaction can be carried on in the actual shell of use or in a shaped vessel shell that can later be dissolved away, if desired. The process also includes steps for the removal of unwanted high molecular weight fractions of PVP prior to heat treatment. The processing of the material to equilibrium volume of the present invention enables the material to maintain its initial volume. This is an important factor in the manufacture of implant products.

It has been found that various embodiments of the cross-linked PVP or PVP derivative, which makes up the cohesive mass, have a variety of additional medical uses. In this regard, for example, the material in sheet form can be utilized to prevent adhesions after surgical procedures by placing a sheet between the organs and the incision site. This property may be enhanced by removing additional water from sheets of the cohesive mass composition by heating or freeze drying. The material is also capable of being extruded through a syringe needle and injected by bolus injection as a filler for tissue or as a carrier for drugs or other therapeutic agents in treatment of human subjects.

DETAILED DESCRIPTION

As indicated, previous literature demonstrates that the cross-linking of PVP must take place in the presence of cross-linking agents or compounds such as cyclic acid amides; and previous literature indicates that the cross-linking of PVP must take place at temperatures of 100° C. or higher. Prior formulations of PVP incorporate between 4% and 25% by weight of PVP in water, and the swellable gels which can be formed in these processes do not have viscosities approaching even 15,000 cp. It was, therefore, unexpected that the present invention could result in a highly elastic, extremely viscous, hydrophilic, swellable, cohesive mass with controlled rates of the cross-linking or other reaction occurring generally of ambient temperature nominally 20° C.-30° C. This occurs without any commercial "cross-linker" and only a minor amount, <1%, by weight (based on the weight of PVP) of a base such as sodium hydroxide added to the initial water solution; and the weight of PVP in the solution is preferably above about 65% to about 80% of the weight of the water, although an excess of PVP can be used.

The above formulation for the cross-linked PVP mixture of the present invention has been physically mixed and compounded and measurements of essential physical characteristics such as viscosity, pH, weight, and freezing point depression of the invented mixture have been recorded. The present formulation was designed to improve the viscosity, cohesiveness, elasticity, and eliminate any problem that might occur from hypertonic formulations that had been previously recorded in the literature as increasing the volume and weight of implanted breast implants. For example *"Long Term Results of MISTI Gold Breast Implants: A Retrospective Study"*, Hildegunde Piza-katzer, MD., et. al., Plastic and Reconstructive Surgery, November 2002. The formula of the present invention has resulted in forming a hydrogel that is a highly viscous very cohesive and elastic mass of cross-linked PVP. The process material is insoluble in water, is radiolucent characteristics material may have a surface that is smooth and may have a satin-like texture. It has been found that the gel can be extruded through a syringe needle and can even be processed in situ in the needle. The material also does not support bacterial growth.

As indicated above, an important aspect of the present invention is the process for producing the cohesive mass or hydrogel of the invention. The process involves dissolving a known minor amount of a base material, preferably solid sodium hydroxide (NaOH) in a known amount of water and thereafter dissolving a known amount of polyvinylpyrrolidone (PVP) such as K 29/32 Plasdone, which is a well known, readily available commercial product in the solution. The solution is thoroughly mixed and allowed to react at ambient temperature and pressure for about 20-60 hours. It should be noted that preferable results are obtained when the weight ratio of the sodium hydroxide to PVP is <1% and wherein the weight of PVP is above 65% of the weight of water. More preferably, the weight of PVP is a minimum of 72% of the weight of water and, most preferably, about 75%. The reacted material is in the form of a cohesive, water-insoluble gel that has a basic pH and is somewhat hydrophilic.

This intermediate material is further processed to form the final gel or cohesive mass in accordance with the invention. This involves a stabilizing step in which the gel formed in the previous step is exposed to an amount of water which, when absorbed by the gel material, swells the gel material while, at the same time, stabilizing the gel to a maximum or equilibrium volume with respect to its hydrophilic nature. Thus, in this step, the gel is seen to swell a certain amount as it takes on water by absorption until its hydrophilic nature is satisfied and it becomes stabilized in volume. The volume-stabilizing aspect is important for many uses of the gel material inasmuch as swelling of the gel as it takes on additional water in certain implanted uses is highly undesirable. Thus, the establishment of volume stability prior to final use may be quite important.

It has been found that the reacted water-insoluble gel mass will absorb from about 25% to 30% by weight of water to become stabilized in volume. Several experimental batches utilizing the process of the present invention resulted in the water-insoluble gel mass absorbing about 27% by weight of water to become stabilized in volume.

As indicated above, a neutralization step may be utilized separately or as part of the hydrolyzing/stabilizing step mentioned above. Depending on the pH acquired by the insoluble gel mass, an acidic or basic solution may be utilized to neutralize the water-insoluble gel mass. Preferentially, the resulting product should have a pH of about 7.0±0.6. The gel produced by the product of the present invention has generally been found to be basic in nature and, accordingly, it has been found that a solution of hydrochloric acid (HCl) can most conveniently be used to neutralize the product. A solution of HCl having a pH of 1.0 or less has been used to neutralize the material.

In conjunction with the present invention, it should be noted that the precise chemical reactions that occur during the processing of the PVP in accordance with the process of the present invention are somewhat unclear. As far as it is presently understood, it is believed that the PVP polymer undergoes chemical changes during the reaction step. These changes are believed to involve opening of the lactam ring that is part of the original PVP polymer, resulting in the formation of amino acid groups that are incorporated into the "modified" polymer. Thus, in this case, of course, the reacted polymer may no longer be a simple PVP structure. It may be a PVP that has been modified to create new chemical moieties incorporated into the polymer structure. Such modifications may likely be responsible for the ability of the material to possess its gel-like properties. This being the case, as indicated, references to cross-linked PVP herein, with respect to the materials produced by the present process are meant to include such modifications of PVP or derivatives of PVP as might occur as a result of the process of the invention.

According to an important aspect of the present invention, it has been found that the length of time the mixture is allowed to react at ambient temperature precisely results in a viscosity that can be controlled to be anywhere between the viscosity of the beginning mixture (approximately 900-1000 cp) to viscosity of the cross-linked PVP viscous cohesive mass (up to about 45,000 cp). It has been determined that the viscosity of the initial formulation can be increased in a controllable manner by the treatment over a period of time. The cohesiveness is increased in a controllable manner, and any osmotic pressure effect becomes irrelevant as the viscosity is increased in the formation of the water-insoluble gel mass.

It has been demonstrated, for example, that a viscosity greater than 10,000 and normally from 15,000 centipoise and up to about 45,000 centipoise maximum cohesiveness and elasticity of the cross-linked PVP cohesive mass is achieved. It appears that any osmolarity effect is almost irrelevant at this level of viscosity and cohesiveness because the cross-linked insoluble PVP cohesive mass does not appear to have a significant osmotic pressure. Thus, the composition has essentially all of the PVP cross-linked or otherwise entrapped in the viscous cohesive mass structure which results in low or no osmotic pressure.

In addition, by water addition, the hydrophilic nature has been stabilized; therefore, water does not move in or out of a device such as through the silicone membrane of a breast implant, or the like, in response to the higher osmotic pressure of the tissue fluids. This of course is a very significant factor and a great improvement in PVP filling materials for breast implants.

The above properties are all desirable characteristics for a breast implant filling material and such a filling material will eliminate several negative aspects of filling materials previously used. Sodium bicarbonate may be substituted for Sodium hydroxide in the initial mixture with the identical PVP cross-linked hydrogel being formed. It is contemplated that other ionic molecules may also occur to those skilled in the art to be substituted for sodium bicarbonate. It will be appreciated that the general process for making the above-described cohesive mass has useful applications in various medical fields. Some of these will be described.

Another aspect of the invention involves the addition of particulate matter to the gel mass. It can be added as contained in a therapeutically active material or alone. Thus, biocompatible particles having a diameter from about 80 microns to about 500 microns can be used, for example. Compounds such as polysiloxanes or other compatible compounds can be used.

First Embodiment

First, the reactive mixture of NaOH and PVP in water in a desired ratio is prepared. The materials must be mixed thoroughly and the mixture degassed, if needed. The mixture is then introduced into an implant shell, such as any silicone shell for a penile implant or breast implant or any kind of an anatomical implant that can be filled with this mixture. In the next step, the material is allowed to react in the implant shell at ambient temperature and pressure for a sufficient period of time to cause the amount of cross-linking of the PVP which is desired for that particular implant. A volume of that mixed fluid solution less than that sufficient to fill a thin silicone implant shell is then introduced into such a shell. Next, that solution in the silicone container or shell is allow to react for a period of 20+ hours at ambient temperature. The filling material will complete its cross-linking in this time at this temperature and will retain its initial weight, volume and shape as a viscous cohesive mass and thereafter an amount of water solution is introduced and the material swells to a size sufficient to fill the shell of interest and, upon sterilization, and normally neutralization, will be ready for use as an anatomical implant.

Second Embodiment

The previous embodiment of the process requires a mold or container and pre-supposes that the mold or container for the gel-like cohesive mass which will be formed will be implanted as part of the anatomical implant, breast implant or penile implant. This, however, is optional and so is not a necessary characteristic of the process of the invention. The formulation of water, PVP and sodium hydroxide as mixed can be optionally introduced into a mold other than a mold that will be utilized as a membrane container for the implant. As an example of an alternate mold, one should be able to make a mold of sodium bicarbonate crystals, introduce the fluid and surround the fluid by the sodium bicarbonate mold and then proceed with the process of reacting the fluid in the mold at ambient temperature and pressure. The desired cohesive mass formed by cross-linking PVP molecules is then subjected to a neutralizing and/or stabilizing step to fill out the mold. The mold can be released by physical means, or in the case of sodium bicarbonate, the mold can be dissolved away with water and the insoluble cohesive mass composition could be retrieved. The water solution used to dissolve the sodium bicarbonate would not dissolve the cross-linked PVP and the remaining material retrieved and recovered would be the cohesive mass of insoluble cross-linked PVP in the molded shape that was desired.

Third Embodiment

In the previous examples, the viscous cohesive mass of water-insoluble, cross-linked PVP material made according to the process when stabilized, and normally neutralized, maintained its initial volume. In some cases for medical use it is desirable to create a scaffolding of PVP, which maintains its original shape but contains little water. It has been found that a modified sheet form of the viscous cohesive mass of cross-linked insoluble PVP gel-like material of the present invention can be utilized to prevent adhesions after a surgical procedure by placing the sheet between the organs and an incision site (see the Second Embodiment). In addition, in another field of medicine, it would be useful to have a PVP sheet similar to that described, with additional water removed from the sheet to provide a scaffold that would induce and be a suitable scaffold to promote cellular growth either outside or inside the body, in vitro or in vivo.

Accordingly, it is a further aspect of the present invention to provide a procedure that will produce such a sheet structure that is substantially devoid of water. In this case, an appropriate volume of PVP such as K-30 PVP, water, and appropriate weight of sodium hydroxide, as in the above examples, would be mixed thoroughly and degassed. The fluid mixture would be poured into a container to form a sheet of the desired thickness, which might be approximately one tenth of an inch, or one quarter of an inch, or even one half of a inch thick.

The poured mixture would then be reacted as above. At this time a viscous cohesive mass of PVP, insoluble in water, would have formed. The sheet would then be freeze-dried by placing the sheet at a freezing temperature in a vacuum chamber and maintaining those conditions until essentially all the water was removed from the sheet in a well-known manner. Alternatively, substantially all of the water could be removed or driven off from the cohesive mass composition sheet by increasing the temperature (heating in an oven).

Appropriate portions of the freeze-dried sheet in combination with the proper nutrients can be used in vitro or in vivo to grow various mammalian cells. Freeze-drying the cohesive mass in sheet form will maintain and preserve the initial shape of the sheet. If the viscous cohesive mass in sheet form is not freeze-dried, but heat is continued to be applied to the viscous cohesive, insoluble PVP sheet, the trapped water will be driven off and the sheet will become a hard or solid sheet of 20-40 percent of the initial volume of the hydrated gel-like sheet. This method for making solid articles that have more solid properties by driving off the water with vacuum or heat also can be employed when a more solid implant material is desirable.

Fourth Embodiment

For some medical uses it is desirable to have a material such as the PVP described previously injected as filler for tissue. For instance, in the field of urology, the viscous cohesive mass made by the process of the present invention may be used as a bulking material that is introduced to the inside of a sphincter muscle by being injected from a syringe. Such a bulking material is also used for filling tissue in scars, dents of the skin, and for remodeling chins, noses, lips, ears, etc. For this procedure, a formulation of soluble PVP, water and sodium hydroxide can be introduced into syringes of 1, 2, and 3 cc volumes, for example. The formulated fluid of PVP would be cross-linked inside the syringes for a length of time sufficient to enable the desired amount of cross-linking of PVP to occur within the syringe to attain an appropriate viscosity for injection in soft tissues. Thus, a viscosity consistent with that of other materials (injectable bulking materials) could be achieved. This would be a viscosity in excess of 15,000 cp. The reacted material would then be subjected to a stabilizing, and normally neutralizing, process. Depending on the formulation and conditions under which the cohesive mass is processed and injected, the cohesive cross-linked mass should remain at the site of injection for an indeterminate period, providing permanent or semi-permanent bulking. If small particles of synthetic biocompatible material such as dimethylsiloxane are added to the material, the particles will remain as a permanent bulking agent.

FIFTH EMBODIMENT

The object of this novel embodiment is to increase the surface area of the volume of cross-linked PVP material. The first step is to form a substantial volume of the viscous cohesive mass of cross-linked PVP composition such as was described in the Second Process Embodiment. A volume of water is added to the volume of viscous cohesive mass of material in a desired selected ratio, such as 1:1. The cohesive mass, which is insoluble in water, is then mechanically broken into pieces using a vigorous, mechanical disruption means such as a blender, for example. Because each of the small pieces created is hydrophilic on its entire surface, the mixture will become as a fluid that can be used to coat tissue surfaces such as internal organs. In addition to the sheet forms indicated above, such a fluid can be used to coat tissue and organ surfaces during and after surgical procedures to form a barrier that reduces unwanted adhesions between the operative site and internal tissue and organs. This fluid can be administered as a spray or as an injectable depending upon the needs of the surgeon to prevent adhesions.

Sixth Embodiment

This aspect or embodiment of the process of the invention makes use of the higher molecular weight commercial material. As indicated, the PVP selected is comprised of large molecules, in excess of 100,000 molecular weight. For example, K-60 or K-90 PVP is used to produce a viscous cohesive mass of cross-linked PVP having a viscosity in excess of 15,000 cp up to about 45,000 cp. This hydrophilic material, while highly viscous, can be introduced into a joint using a syringe and needle delivery system. The material is also lubricious and, in this manner, will serve as a lubricant for joint surfaces.

Seventh Embodiment

It is contemplated that the cross-linked PVP material made by the process of the present invention can advantageously be employed for still other medical uses. For example, for some medical uses it would be desirable to have a material such as the cross-linked PVP described in relation to the process of the Second Embodiment, for example, that can be used as a drug delivery system. For instance a drug may advantageously be mixed with a substantial volume of the viscous cohesive mass of cross-linked PVP material such as described in the Second Embodiment. The gel-like material and drug mixture can then be placed in contact with the body as through injection as a bolus, transdermally through contact with the skin or by other well known means. Typically, the drug will migrate out of the cohesive mass and be made available to the body. For example, a PVP viscous cohesive mass was prepared as in the Second Embodiment process and a red, water-soluble, food dye was incorporated into the formulation. The now-colored gel-like insoluble material was placed into a container containing water and allowed to remain in contact with the water. After time, the water became colored red, indicating transfer of dye from the insoluble cohesive mass into the water phase. In another example, a PVP material was prepared using the process of the Second Embodiment and placed into a container containing a water solution of a red, water-soluble, food dye. After time, the bolus of the insoluble composition was removed from the water solution and observed. Quantities of the red dye had migrated into the insoluble cohesive mass. These examples demonstrate that pharmacologically active materials could be delivered to the body via migration into or out of the cohesive mass of cross-linked PVP produced in accordance with the invention.

The procedure of the present invention allows the formulation of insoluble PVP in volumes and shapes that are desirable for various medical uses. The process of the invention also allows the insoluble PVP to remain a specific volume and shape and form a cohesive viscous mass of material which has not been possible in previous processes that require processing temperatures above 100° C. At processing temperatures above 100° C. water is lost and the volume is reduced, therefore the shape and volume is reduced and unpredictable.

The cohesive mass may be produced in a form that can be injected to augment tissue, in addition to a form that can be used as a filling material in anatomical implants. The composition of the present invention may be used in many other applications that require a cohesive gel.

The combination of water-insoluble cohesive gel mixed with PVP soluble in water can be used as an injectable material. Because PVP in the soluble form or in the water-insoluble form is biocompatible and does not illicit a immunological allergenic reaction in the body, the medical devices described previously can be comprised of PVP that has been treated in the manner described to become water-insoluble in the form of a cohesive water-insoluble composition, or the cohesive water-insoluble PVP material can be used in combination with PVP water soluble fluid. A combination of water-soluble and water-insoluble PVP can be used for a biocompatible anti-adhesion composition and in various other medical devices.

This invention has been described herein in considerable detail in order to comply with the patent statutes and to provide those skilled in the art with the information needed to apply the novel principles and to construct and use such specialized components as are required. However, it is to be understood that the invention can be carried out by specifically different equipment and devices, and that various modifications, both as to the equipment and operating procedures, can be accomplished without departing from the scope of the invention itself.

What is claimed is:

1. A material suitable for use in an implant consisting of a biocompatible water-insoluble, hydrophilic flexible cohesive elastic aqueous polyvinylpyrrolidone (PVP) gel mass free of cross-linking agents and having a volume that is water-stabilized wherein said implantable material is obtained by:
   (a) combining an amount of water with an amount of polyvinylpyrrolidone (PVP) having a molecular weight-related viscosity of K 29 or greater and wherein the weight of PVP is about 65% to about 80% of the weight of the water, and a minor amount of base compound forming a mixture wherein the mixture is free of cross-linking agents;
   (b) reacting the mixture of (a) at ambient temperature and pressure until a hydrophilic flexible cohesive water-insoluble gel mass is formed; and
   (c) adding an amount of water to the reacted gel mass of (b) to maximize and stabilize the gel mass volume.

2. A material as in claim 1 wherein the pH of the stabilized gel mass is 7.0±0.6.

3. A material as in claim 1 wherein the material is contained in an implantable elastomeric container.

4. A material as in claim 1 including an amount of therapeutically active material infused into the gel mass.

5. A material as in claim 4 wherein the therapeutically active material includes biocompatible particles having a diameter of from 80 microns to 500 microns.

6. A material as in claim 1 wherein in step (a) the weight of the amount of PVP is from about 72% to about 80% of the weight of the amount of water.

7. A material as in claim 1 wherein said molecular weight-related viscosity is K 29/32.

8. A material as in claim 1 wherein in step (a) the amount of PVP is about 75% of the weight of the water.

9. A material as in claim 1 wherein said base compound is NaOH.

10. A material as in claim 9 wherein the weight of said base compound is from about 0.1% to 1% of the weight of the PVP, 11. A material suitable for use in an implant consisting of a biocompatible water-insoluble, hydrophilic, flexible, cohesive elastic aqueous polyvinylpyrrolidone (PVP) gel mass free of cross-linking agents and having a volume that is water-stabilized wherein said implantable material is obtained by:
  (a) forming a mixture consisting of an amount of water combined with an amount of polyvinylpyrrolidone (PVP) having a molecular weight-related viscosity of K 29/32 or greater and wherein the weight of PVP is about 72% to about 80% of the weight of the water, and a minor amount of sodium hydroxide (NaOH) base compound;
  (b) reacting the mixture of (a) at ambient temperature and pressure until a hydrophilic flexible cohesive elastic water-insoluble gel mass is formed; and
  (c) adding an amount of water to the reacted gel mass of (b) to maximize and stabilize the gel mass volume.

12. A material as in claim 11 wherein the viscosity-average value of molecular weight of the PVP is $\geqq 40,000$.

* * * * *